United States Patent
Murata et al.

(10) Patent No.: US 7,772,280 B2
(45) Date of Patent: Aug. 10, 2010

(54) CRYSTALS OF L-ORNITHINE AND PROCESS FOR PRODUCING THE SAME

(75) Inventors: Hideki Murata, Hofu (JP); Ikuhiro Nakatani, Hofu (JP); Mariko Shitashige, Shunan (JP); Kenji Tajima, Hofu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 696 days.

(21) Appl. No.: 11/719,122

(22) PCT Filed: Nov. 14, 2005

(86) PCT No.: PCT/JP2005/020812

§ 371 (c)(1),
(2), (4) Date: May 11, 2007

(87) PCT Pub. No.: WO2006/051940

PCT Pub. Date: May 18, 2006

(65) Prior Publication Data

US 2009/0082594 A1 Mar. 26, 2009

(30) Foreign Application Priority Data

Nov. 15, 2004 (JP) .............................. 2004-330107

(51) Int. Cl.
*A61K 31/195* (2006.01)
*C07C 227/00* (2006.01)
*C07C 229/00* (2006.01)

(52) U.S. Cl. ........................ 514/564; 562/554; 562/561

(58) Field of Classification Search ........................ None
See application file for complete search history.

(56) References Cited

U.S. PATENT DOCUMENTS 3,028,424 A 4/1962 Kline
4,228,099 A * 10/1980 Walser ........................ 562/560
4,420,432 A 12/1983 Chibata et al.
4,714,767 A 12/1987 Tanaka et al.
5,227,007 A 7/1993 Tateba et al.
2003/0099760 A1 5/2003 Okai

FOREIGN PATENT DOCUMENTS

EP 0714884 5/1996
FR 1481195 * 5/1967
JP 46003194 B 1/1971
JP 50135281 A 10/1975

OTHER PUBLICATIONS

Merck, The Merck Index, 10th edition, 1983, Merck & Co., Inc., Rahway, NJ, pp. 985-986.*
Kurtz, "A Simple Synthesis of dl-Citrulline", J. Biol. Chem., vol. 122, No. 2 (1938) 477-84.
Vickery and Cook, "The Preparation of Crystalline Ornithine. The Picrates and Monosulfates of Ornithine", J. Biol. Chem., vol. 94, No. 2 (1931) 393-99.
Warning and Jensen, "A Facile Synthesis of αω-Diaminocarbonsäuren (Lysine, Ornithine)", Justus Liebigs Annalen der Chemie (1978) 1707-12.

* cited by examiner

*Primary Examiner*—Paul A Zucker
(74) *Attorney, Agent, or Firm*—Fitzpatrick, Cella, Harper & Scinto

(57) ABSTRACT

The present invention provides crystals of L-ornithine and a process for producing the crystals of L-ornithine including the steps of (i) exposing L-ornithine or a salt thereof, a composition comprising L-ornithine or a salt thereof, or a solution containing L-ornithine, a salt thereof, or the composition to a cation exchange resin to adsorb L-ornithine onto the cation exchange resin; (ii) eluting L-ornithine from the cation exchange resin on which L-ornithine is adsorbed with an aqueous alkaline solution, and removing an alkaline component from the resulting eluate to prepare an aqueous L-ornithine solution; and (iii) mixing the aqueous L-ornithine solution with a hydrophilic organic solvent, and crystallizing L-ornithine from the resulting mixed solution.

17 Claims, No Drawings

CRYSTALS OF L-ORNITHINE AND PROCESS FOR PRODUCING THE SAME

TECHNICAL FIELD

The present invention relates to crystals of L-ornithine (L-ornithine crystals) and a process for producing the same.

BACKGROUND ART

L-ornithine has been widely used as an ingredient of nutrition enriching additives, pharmaceuticals or the like.

Since it is difficult to prepare a free base of L-ornithine as crystals, it is available usually in the form of a salt such as hydrochloride (Product Catalogue 2004 to 2005 of Sigma).

When L-ornithine is used as an ingredient of a transfusion or the like for the purpose of nutrition enriching or the like, for example, by using it in the form of hydrochloride as it is, an acidosis symptom may be induced. Also, administration of a transfusion containing a large amount of chlorine ions is unfavorable for patients with a renal disease in particular. It has also been well known that when L-ornithine is used either by being mixed in foods or the like as a nutrition enriching additive or the like or orally as it is, it is difficult to utilize the same in the form of, for example, hydrochloride because of its bitter taste. Thus, there is a demand for L-ornithine as a free base. However, as described above, it is difficult to prepare L-ornithine crystals. In general, amorphous forms of amino acids are highly hygroscopic and are not preferred as distribution forms. Hence, there is a demand for L-ornithine crystals in a satisfactory distribution form and a process for producing the L-ornithine crystals.

Although use of an aqueous solution of free base of L-ornithine (aqueous L-ornithine solution) has already been known, a method for preparing L-ornithine crystals from the aqueous L-ornithine solution has not been known (see Patent Documents 1 to 3). It is known that an aqueous solution of free base of an amino acid including L-ornithine can thoroughly be dried to give crystals of the free base of amino acid. However, there is no specific description of L-ornithine crystals (see Patent Document 4).

Patent Document 1: Japanese Published Examined Patent Application No. 3194/1971
Patent Document 2: Japanese Published Unexamined Patent Application No. 364155/1992
Patent Document 3: Japanese Published Unexamined Patent Application No. 136254/1980
Patent Document 4: Japanese Published Unexamined Patent Application No. 144088/2003

DISCLOSURE OF THE INVENTION

Problems to be Solved by the Invention

An object of the present invention is to provide crystals of an L-ornithine excellent as a supply source of L-ornithine and a process for producing the same.

Means for Solving the Problem

The present invention relates to the following (1) to (11):
(1) Crystals of L-ornithine.
(2) The crystals according to (1) wherein the content of L-ornithine is 95% by weight or more.
(3) A process for producing crystals of L-ornithine, comprising the step of eluting L-ornithine from a cation exchange resin on which L-ornithine is adsorbed with an aqueous alkaline solution, and removing an alkaline component from the resulting eluate to prepare an aqueous L-ornithine solution.
(4) A process for producing crystals of L-ornithine, comprising the step of mixing an aqueous L-ornithine solution with a hydrophilic organic solvent and, crystallizing L-ornithine from the resulting mixed solution.
(5) A process for producing crystals of L-ornithine, comprising the steps of: (i) exposing L-ornithine or a salt thereof, a composition comprising L-ornithine or a salt thereof, or a solution containing L-ornithine, a salt thereof, or the composition to a cation exchange resin to adsorb L-ornithine onto the cation exchange resin; (ii) eluting L-ornithine from the cation exchange resin on which L-ornithine is adsorbed with an aqueous alkaline solution, and removing an alkaline component from the resulting eluate to prepare an aqueous L-ornithine solution; and (iii) mixing the aqueous L-ornithine solution with a hydrophilic organic solvent, and crystallizing L-ornithine from the resulting mixed solution.
(6) The process according to (5), wherein the solution containing L-ornithine, a salt thereof, or the composition comprising L-ornithine or a salt thereof is a culture solution of L-ornithine.
(7) The process according to (3), (5) or (6), wherein the aqueous alkaline solution is aqueous ammonia.
(8) The process according to any one of (3) and (5) to (7), wherein the step of removing an alkaline component from the resulting eluate is the concentration of the eluate.
(9) The process according to any one of (4) to (8), wherein the hydrophilic organic solvent is a solvent selected from the group consisting of methanol, ethanol, propanol, isopropyl alcohol, n-butanol, ethylene glycol, acetone, acetonitrile, N,N-dimethylformamide and N,N-dimethylacetamide.
(10) The process according to any one of (4) to (8), wherein the hydrophilic organic solvent is methanol or ethanol.
(11) A method for purifying L-ornithine, comprising the steps of: (i) exposing L-ornithine to a cation exchange resin to adsorb L-ornithine onto the cation exchange resin, (ii) eluting L-ornithine from the cation exchange resin on which L-ornithine is adsorbed with an aqueous alkaline solution, and removing an alkaline component from the resulting eluate to prepare an aqueous L-ornithine solution, and (iii) mixing the aqueous L-ornithine solution with a hydrophilic organic solvent, and crystallizing L-ornithine from the resulting mixed solution.

EFFECT OF THE INVENTION

The present invention provides crystals of L-ornithine excellent as a supply source of L-ornithine and a process for producing the same.

BEST MODE FOR CARRYING OUT THE INVENTION

The content of L-ornithine in L-ornithine crystals according to the present invention is preferably 95% by weight or more, and more preferably 97% by weight or more. The L-ornithine crystals may contain less than 5% by weight and preferably less than 3% by weight of water. Furthermore, the L-ornithine crystals may contain less than 5% by weight and preferably less than 3% by weight of a hydrophilic organic solvent, such as methanol, ethanol, propanol, isopropyl alcohol, n-butanol, ethylene glycol, acetone, acetonitrile, N,N-dimethylformamide, N,N-dimethylacetamide or the like.

L-ornithine crystals according to the present invention may have a plurality of crystalline forms. L-ornithine crystals according to the present invention include all of these crystalline forms.

The alkaline component in the present invention is an alkaline component other than L-ornithine contained in the eluate, for example, which is obtained by eluting L-ornithine from an L-ornithine-adsorbed cation exchange resin eluted with an aqueous alkaline solution. More specifically, the alkaline component in the present invention is, for example, sodium hydroxide for an eluate containing sodium hydroxide (for example, elution with an aqueous sodium hydroxide solution), sodium carbonate for an eluate containing sodium carbonate (for example, elution with an aqueous sodium carbonate solution), and ammonia for an eluate containing ammonia (for example, elution with an aqueous ammonia).

A process for producing L-ornithine crystals according to the present invention is described below.

The raw material of the process for producing L-ornithine crystals according to the present invention includes various forms of L-ornithine, for example, L-ornithine or a salt thereof, compositions comprising L-ornithine or a salt thereof, solutions containing L-ornithine, a salt thereof or the composition, such as aqueous solutions (L-ornithine solutions), cation exchange resins on which L-ornithine is adsorbed, and the like. L-ornithine contained in the raw materials may be produced by any method such as a fermentation method, a chemical synthesis method, and a fermentation method in combination with a chemical synthesis method.

The salts of above-mentioned L-ornithine include L-ornithine hydrochloride (SIGMA-ALDRICH Corp., Product catalog 2004-2005), L-ornithine L-aspartate (Japanese Unexamined Published Patent Application No. 364155/1992), L-ornithine malate (Japanese Published Unexamined Patent Application No. 136254/1980), L-ornithine succinate (CAS Registry No. 24870-67-5) and the like.

The compositions comprising L-ornithine or a salt thereof may include any composition comprising the above-mentioned L-ornithine or a salt thereof, but not be limited to. For example, the compositions comprising L-ornithine or a salt thereof include fermentation products containing L-ornithine (for example, a mixture of L-ornithine with a bacterial cell, an acid, a base, an inorganic salt, a solvent and the like), mixtures of L-ornithine and substances used in the production of L-ornithine (for example, a mixture of L-ornithine and a solvent, an inorganic salt used in the production of L-ornithine and the like), and compositions comprising the salt of L-ornithine described above and the like.

The L-ornithine solutions may include any solution in which above-mentioned L-ornithine, a salt thereof, or the composition comprising L-ornithine or a salt thereof is dissolved in water, a hydrophilic organic solvent or a mixed solvent thereof, but not be limited to. For example, aqueous L-ornithine solutions, aqueous solutions containing L-ornithine in which commercially available L-ornithine hydrochloride or the like is dissolved, culture solutions of L-ornithine obtained by a fermentation method and the like are included. Preferably, the L-ornithine solution is a culture solution of L-ornithine.

The above-mentioned culture solution of L-ornithine used in the present invention may be obtained, for example, by a conventional fermentation method. Specifically, an L-ornithine-producing bacterium, for example, Corynebacterium glutamicum, Corynebacterium acetoacidophilum, Corynebacterium Herculis, Corynebacterium lilium, Brevibacterium divaricatum, Brevibacterium flavum, Brevibacterium immariophilum, Brevibacterium lactofermentum, Brevibacterium thiogenitalis or the like is cultured in a common culture medium containing a carbon source, a nitrogen source, an inorganic salt, a vitamin and the like under aerobic conditions while the temperature and the pH are appropriately controlled. L-ornithine is produced and is accumulated in the culture. Thus, the culture solution of L-ornithine can be obtained from the culture. The above-mentioned culture medium may be either a synthetic medium or a natural medium, provided that the culture medium contains nutrients essential for the growth of an L-ornithine-producing bacterium and the biosynthesis of L-ornithine, such as a carbon source, a nitrogen source, an inorganic salt and a vitamin. The carbon source may be any carbon source that can be assimilated by microorganisms. Examples of the carbon source include saccharides, such as glucose and fructose, alcohols, such as ethanol and glycerol, and organic acids, such as acetic acid. Examples of the nitrogen source include ammonium salts, such as ammonia and ammonium sulfate, nitrogen compounds, such as amines, and natural nitrogen sources, such as peptone and soybean hydrolysates. Examples of the inorganic salt include potassium phosphate, magnesium sulfate, sodium chloride, ferrous sulfate, potassium carbonate and the like. Examples of the vitamin include biotin, thiamine and the like. In culture, a substance required for the growth of an L-ornithine-producing bacterium (for example, a required amino acid for a microorganism requiring an amino acid) may be added as needed. Preferably, the culture can be performed under aerobic conditions, such as by shaking culture or by aeration spinner culture. The incubation temperature is 20° C. to 50° C., preferably 20° C. to 42° C., and more preferably 28° C. to 38° C. The incubation pH is 5 to 9 and preferably 6 to 7.5. The incubation period is 5 hours to 5 days and preferably 16 hours to 3 days. A culture solution and bacterial cells can be separated from the culture by a conventional method. For example, when a culture solution and bacterial cells are separated by filtration or centrifugation, Nutsche, filter press or Laval centrifuge may be utilized. Preferably, the pH of the culture is adjusted to 1.5 to 3.8 and preferably to 1.5 to 1.8 by adding hydrochloric acid, sulfuric acid or nitric acid and preferably by adding sulfuric acid.

A process for producing L-ornithine crystals according to the present invention includes at least one step selected from (i) a step of exposing L-ornithine or a salt thereof, a composition comprising L-ornithine or a salt thereof, or a solution containing L-ornithine, a salt thereof or the composition to a cation exchange resin to adsorb L-ornithine onto the cation exchange resin, (ii) a step of eluting L-ornithine from a cation exchange resin on which L-ornithine is adsorbed with an aqueous alkaline solution, and removing an alkaline component from the resulting eluate to prepare an aqueous L-ornithine solution, and (iii) a step of mixing an aqueous L-ornithine solution with a hydrophilic organic solvent, and crystallizing L-ornithine from the resulting mixed solution.

(i) The step of exposing L-ornithine or a salt thereof, a composition comprising L-ornithine or a salt thereof, or a solution containing L-ornithine, a salt thereof or the composition to a cation exchange resin to adsorb L-ornithine onto the cation exchange resin is a step of being adsorbed L-ornithine containing in the above-mentioned L-ornithine or a salt thereof, the composition comprising L-ornithine or a salt thereof, or the L-ornithine solution onto the cation exchange resin. Specifically, for example, the above-mentioned L-ornithine solution or the solution being dissolved L-ornithine or a salt thereof or the composition comprising L-ornithine or a salt thereof in a solvent, such as water or an organic solvent, is passed through a column packed with a cation exchange resin to adsorb L-ornithine onto the cation exchange resin. After being passed the L-ornithine solution or the solution through a column, the cation exchange resin is preferably washed, for example, with water as needed. Examples of the cation exchange resin include a strongly acidic cation exchange resin and specifically a gel-type strongly acidic cation exchange resin composed of a styrene-divinylbenzene copolymer and having a sulfonyl group as an exchangeable group. More specifically, examples of the cation exchange resin include Dowex HCR-S, Dowex HCR-W2, Dowex HGR-W2, and Dowex Marathon C (manufactured by The Dow Chemical Company), and DIAION SK1B, DIAION SK102, DIAION SK104, DIAION SK110, DIAION SK112 and DIAION SK116 (manufactured by Mitsubishi Chemical Corporation).

(ii) The step of eluting L-ornithine from a cation exchange resin on which L-ornithine is adsorbed with an aqueous alkaline solution, and removing an alkaline component from the resulting eluate to obtain an aqueous L-ornithine solution is a step of eluting L-ornithine, for example, from a cation exchange resin on which L-ornithine is adsorbed preferably by the method in the above step (i) with an aqueous alkaline solution, and removing an alkaline component from the resulting eluate to obtain an aqueous L-ornithine solution. Examples of the aqueous alkaline solution include 1 to 6 mol/L, preferably 1 to 3 mol/L aqueous solutions of inorganic bases, such as sodium hydroxide, potassium hydroxide, sodium carbonate and potassium carbonate, 1 to 6 mol/L, preferably 1 to 3 mol/L aqueous ammonia, and aqueous solutions of 10% to 80% by weight and preferably 10% to 40% by weight of organic amines such as methylamine, dimethylamine and ethylamine. Among these, aqueous ammonia and aqueous solutions of organic amines having low boiling points such as methylamine and dimethylamine are preferred. Aqueous ammonia is more preferred.

The aqueous L-ornithine solution can be prepared by neutralizing an eluate containing L-ornithine eluted with the above-mentioned aqueous alkaline solution, for example, with hydrochloric acid, sulfuric acid or acetic acid to the isoelectric point of L-ornithine (removing of alkaline components). It is preferable to desalt the resulting solution before using it in the next step (iii). The desalination may be performed by a conventional method.

By using the above preferred aqueous alkaline solution such as aqueous ammonia to elute, dissolved alkaline components, such as ammonia, can be removed simply by concentrating the eluate under reduced pressure. Thus, the aqueous L-ornithine solution can easily be prepared. For example, when aqueous ammonia is used as an eluting solvent, the aqueous L-ornithine solution can be obtained by concentrating an eluate under normal pressure or under reduced pressure. The vacuum concentration is performed at a pressure preferably of 140 mmHg or less and more preferably of 40 mmHg or less and at a temperature preferably between 20° C. and 80° C. and more preferably between 40° C. and 50° C. It is preferred that the eluate is concentrated to the L-ornithine concentration, for example, of 200 to 600 g/L and preferably of 300 to 400 g/L.

(iii) A step of mixing an aqueous L-ornithine solution with a hydrophilic organic solvent, and crystallizing L-ornithine from the resulting mixed solution is a step of adding a hydrophilic organic solvent to an aqueous L-ornithine solution preferably obtained by the method in the above step (ii), or adding an aqueous L-ornithine solution preferably obtained by the method in the above step (ii) to an hydrophilic organic solvent, and crystallizing L-ornithine from the resulting mixed solution to obtain L-ornithine crystals.

The aqueous L-ornithine solution may be used any aqueous solution containing a free base of L-ornithine. Preferably, the aqueous L-ornithine solution obtained, for example, in the step (ii) described above can be used as it is, or after being adjusted to a desired concentration as described below. More preferably, the aqueous L-ornithine solution can be used after being decolorized, for example, using activated carbon.

Examples of the hydrophilic organic solvent include methanol, ethanol, propanol, isopropyl alcohol, n-butanol, ethylene glycol, acetone, acetonitrile, N,N-dimethylformamide, N,N-dimethylacetamide and the like. Methanol and ethanol are preferred.

When a hydrophilic organic solvent is added to the aqueous L-ornithine solution, L-ornithine crystals can be obtained, for example, by gradually adding the hydrophilic organic solvent to the aqueous L-ornithine solution preferably obtained in the step (ii) described above with stirring at a temperature between 0° C. and 50° C., preferably between 5° C. and room temperature, and more preferably at room temperature, followed by standing, stirring, and cooling, as needed, and isolating and drying precipitated crystals.

When the aqueous L-ornithine solution obtained in the step (ii) described above is used, it may be used as it is. Preferably, it may be used by adjusting the concentration of L-ornithine, for example, to 600 to 900 g/L, preferably to 800 to 900 g/L, and more preferably to 860 to 880 g/L.

The amount of hydrophilic organic solvent is, for example, 1 to 10 times, preferably 3 to 8 times, and more preferably 4 to 6 times the amount of aqueous L-ornithine solution. Furthermore, after the addition of a hydrophilic organic solvent, the mixture may be stirred, for example, at a temperature between 0° C. and room temperature, and preferably at between 0° C. and 10° C. for 5 minutes to 48 hours to increase the yield of L-ornithine crystals.

The isolating and drying method may be a conventional method. For example, L-ornithine crystals can be obtained by separating precipitated L-ornithine crystals using centrifugation, plate filtration or vacuum filtration with Nutsche, followed by drying under reduced pressure, for example, at a temperature between room temperature and 50° C., and preferably at room temperature for 5 to 90 hours, and preferably for 12 to 72 hours.

When an aqueous L-ornithine solution is added to a hydrophilic organic solvent, L-ornithine crystals can be obtained, for example, by gradually adding an aqueous L-ornithine solution preferably obtained in the step (ii) described above to the hydrophilic organic solvent with stirring at a temperature between 0° C. and room temperature, and separating and drying precipitated crystals.

When the aqueous L-ornithine solution obtained in the step (ii) described above is used, it may be used as it is. Preferably, it may be used by adjusting the concentration of L-ornithine, for example, to 600 to 1000 g/L and preferably to 850 to 900 g/L.

The amount of the hydrophilic organic solvent is, for example, 10 to 200 times and preferably 100 to 150 times the amount of aqueous L-ornithine solution to be added. Furthermore, the yield of L-ornithine crystals may be increased by stirring at a temperature between 0° C. and room temperature, and preferably at a temperature between 0° C. and 10° C. for 5 minutes to 48 hours.

The isolating and drying method may be the same as described above.

A method of purification of the present invention can be performed in accordance with the items described in the process of the present invention.

The present invention is specifically described below with reference to Examples. However, the present invention is not limited to these Examples.

EXAMPLE 1

A culture substance of L-ornithine obtained by a method described in Japanese Published Unexamined Patent Application No. 119194/1986 was centrifuged to separate bacterial cells. The resulting culture solution of L-ornithine was passed through a column packed with a strongly acidic ion exchange resin (Marathon C (H type)). After the column was washed with 500 mL of water, L-ornithine was eluted with 1000 mL of 2 mol/L aqueous ammonia. After the eluate was concentrated to a volume of about 200 mL, 2.5 g of activated carbon was added to the eluate. The resulting solution was stirred at 60° C. for 30 minutes. After the activated carbon was filtered off, the filtrate was concentrated to a volume of 70 mL. Ethanol (350 mL) was added dropwise to the resulting concentrate at room temperature with stirring. The resulting mixture was cooled to 5° C. and stirred for 48 hours. Precipitated crystals were collected by filtration and washed with 350 mL of ethanol. Then, the crystals were dried at 20° C. under reduced pressure for 3 days to give L-ornithine crystals as white columnar crystals.

Yield 56.6%.

Melting point (DSC): 150.5° C.

Infrared absorption spectra (KBr, cm$^{-1}$): 1480.3, 1447.5, 1244.0, 1144.7, 933.5

Crystal composition analysis: The results are shown Table 1.

TABLE 1

|  | Found (%) |
|---|---|
| L-ornithine (%)* | 97.48 |
| Water (%)** | 2.63 |
| Ethanol (%)*** | 0.20 |

(Notes)
*Calculated by analyzing L-ornithine via an OPA coloring method (excitation wavelength: 340 nm, fluorescence wavelength: 455 nm) using high-performance liquid chromatography (HPLC).
**Measured by Karl Fisher method.
***Analyzed and calculated by gas chromatography.

X-ray powder diffraction analysis: It is measured with RAD-X type (Rigaku Denki Corporation). The results are shown in Table.

TABLE 2

| Analytical angle (2θ (theta)) | Peak intensity (Relative intensity) |
|---|---|
| 4.95 | 73 |
| 5.30 | 100 |
| 12.15 | 15 |
| 14.95 | 7 |
| 15.25 | 7 |
| 15.95 | 13 |
| 17.70 | 10 |
| 19.45 | 23 |
| 20.00 | 5 |
| 20.85 | 20 |
| 21.25 | 6 |
| 22.00 | 13 |
| 22.40 | 16 |
| 22.65 | 18 |
| 24.05 | 20 |
| 24.45 | 14 |
| 24.95 | 11 |
| 27.15 | 5 |
| 28.35 | 22 |
| 29.00 | 12 |
| 32.25 | 8 |
| 33.80 | 8 |
| 34.20 | 7 |
| 34.95 | 6 |
| 35.95 | 11 |
| 37.15 | 6 |
| 39.00 | 5 |

EXAMPLE 2

As in Example 1, a culture solution of L-ornithine was treated with a strongly acidic ion exchange resin. The resulting eluate was concentrated to a volume of 20 mL, and added dropwise to 500 mL of ethanol at room temperature with stirring. Precipitated crystals were collected by filtration, and washed with 75 mL of ethanol. Then, the crystals were dried at 20° C. under reduced pressure for 3 days to give L-ornithine crystals as white columnar crystals.

Yield 61.1%.

Melting point (DSC): 151.8° C.

Infrared absorption spectra (KBr, cm$^{-1}$): 1480.3, 1447.5, 1244.0, 1144.7, 933.5

Crystal composition analysis: The results are shown in Table 3.

TABLE 3

|  | Found (%) |
|---|---|
| L-ornithine (%)* | 97.08 |
| Water (%)** | 2.03 |
| Ethanol (%)*** | 0.21 |

(Notes)
*Calculated by analyzing L-ornithine via an OPA coloring method (excitation wavelength: 340 nm, fluorescence wavelength: 455 nm) using high-performance liquid chromatography (HPLC).
**Measured by Karl Fisher method.
***Analyzed and calculated by gas chromatography.

X-ray powder diffraction analysis: It is measured with RAD-X type (Rigaku Denki Corporation). The results are shown in Table 4.

TABLE 4

| Analytical angle (2θ (theta)) | Peak intensity (Relative intensity) |
|---|---|
| 5.25 | 100 |
| 12.15 | 9 |
| 15.25 | 4 |
| 15.90 | 15 |
| 17.65 | 6 |
| 19.40 | 14 |
| 20.85 | 9 |
| 22.00 | 7 |
| 22.40 | 8 |
| 22.60 | 9 |

TABLE 4-continued

| Analytical angle (2θ (theta)) | Peak intensity (Relative intensity) |
| --- | --- |
| 24.00 | 16 |
| 24.45 | 6 |
| 24.90 | 5 |
| 27.25 | 2 |
| 27.70 | 2 |
| 28.35 | 11 |
| 28.95 | 11 |
| 32.20 | 5 |
| 34.10 | 6 |
| 34.90 | 8 |
| 37.10 | 3 |
| 38.95 | 3 |

INDUSTRIAL APPLICABILITY

Crystals of L-ornithine (L-ornithine crystals) and a process for producing the same provided in the present invention are useful as the supply source of L-ornithine.

The invention claimed is:

1. Isolated crystals of L-ornithine that have an X-ray powder diffraction pattern expressed in terms of the 2θ shown by (i) or (ii):
    (i) 4.95, 5.30, 12.15, 14.95, 15.25, 15.95, 17.70, 19.45, 20.00, 20.85, 21.25, 22.00, 22.40, 22.65, 24.05, 24.45, 24.95, 27.15, 28.35, 29.00, 32.25, 33.80, 34.20, 34.95, 35.95, 37.15 and 39.00; or
    (ii) 5.25, 12.15, 15.25, 15.90, 17.65, 19.40, 20.85, 22.00, 22.40, 22.60, 24.00, 24.45, 24.90, 27.25, 27.70, 28.35, 28.95, 32.20, 34.10, 34.90, 37.10 and 38.95.

2. A composition, comprising crystals of L-ornithine that have an X-ray powder diffraction pattern expressed in terms of the 2θ shown by (i) or (ii):
    (i) 4.95, 5.30, 12.15, 14.95, 15.25, 15.95, 17.70, 19.45, 20.00, 20.85, 21.25, 22.00, 22.40, 22.65, 24.05, 24.45, 24.95, 27.15, 28.35, 29.00, 32.25, 33.80, 34.20, 34.95, 35.95, 37.15 and 39.00; or
    (ii) 5.25, 12.15, 15.25, 15.90, 17.65, 19.40, 20.85, 22.00, 22.40, 22.60, 24.00, 24.45, 24.90, 27.25, 27.70, 28.35, 28.95, 32.20, 34.10, 34.90, 37.10 and 38.95.

3. The composition according to claim 2, wherein the content of L-ornithine crystals is 95% by weight or more.

4. A process for producing crystals of L-ornithine according to claim 1, comprising, in this order, the steps of:
    obtaining a cation exchange resin on which L-ornithine is adsorbed,
    eluting L-ornithine from said cation exchange resin with an aqueous alkaline solution, and
    removing an alkaline component from the resulting eluate to prepare an aqueous L-ornithine solution.

5. A process for producing crystals of L-ornithine according to claim 1, comprising the steps of:
    mixing an aqueous L-ornithine solution with a hydrophilic organic solvent, and
    crystallizing L-ornithine from the resulting mixed solution.

6. A process for producing crystals of L-ornithine according to claim 1, comprising, in this order, the steps of:
    selecting L-ornithine or a salt thereof, or a solution or a composition comprising L-ornithine or a salt thereof;
    exposing said L-ornithine, L-ornithine salt, composition or solution to a cation exchange resin to adsorb L-ornithine onto the cation exchange resin;
    eluting L-ornithine from the cation exchange resin with an aqueous alkaline solution, and removing an alkaline component from the resulting eluate to prepare an aqueous L-ornithine solution;
    mixing the aqueous L-ornithine solution with a hydrophilic organic solvent; and
    crystallizing L-ornithine from the resulting mixed solution.

7. The process according to claim 6, comprising selecting a solution or composition comprising L-ornithine or a salt thereof, wherein said solution or composition is a culture broth of L-ornithine.

8. The process according to claim 4, 6 or 7, wherein the aqueous alkaline solution is aqueous ammonia.

9. The process according to any one of claims 4, 6 or 7, wherein the step of removing an alkaline component from the resulting eluate is the concentration of the eluate.

10. The process according to any one of claims 5 to 7, wherein the hydrophilic organic solvent is selected from the group consisting of methanol, ethanol, propanol, isopropyl alcohol, n-butanol, ethylene glycol, acetone, acetonitrile, N,N-dimethylformamide and N,N-dimethylacetamide.

11. The process according to any one of claims 5 to 7, wherein the hydrophilic organic solvent is methanol or ethanol.

12. A method for purifying L-ornithine, comprising, in this order, the steps of:
    exposing L-ornithine to a cation exchange resin to adsorb L-ornithine onto the cation exchange resin,
    eluting L-ornithine from the cation exchange resin with an aqueous alkaline solution,
    removing an alkaline component from the resulting eluate to prepare an aqueous L-ornithine solution,
    mixing the aqueous L-ornithine solution with a hydrophilic organic solvent,
    crystallizing L-ornithine from the resulting mixed solution, and
    thereby obtaining crystals of L-ornithine described in claim 1.

13. The process according to claim 8, wherein the step of removing an alkaline component from the resulting eluate is the concentration of the eluate.

14. The process according to claim 8, wherein the hydrophilic organic solvent is selected from the group consisting of methanol, ethanol, propanol, isopropyl alcohol, n-butanol, ethylene glycol, acetone, acetonitrile, N,N-dimethylformamide and N,N-dimethylacetamide.

15. The process according to claim 9, wherein the hydrophilic organic solvent is selected from the group consisting of methanol, ethanol, propanol, isopropyl alcohol, n-butanol, ethylene glycol, acetone, acetonitrile, N,N-dimethylformamide and N,N-dimethylacetamide.

16. The process according to claim 8, wherein the hydrophilic organic solvent is methanol or ethanol.

17. The process according to claim 9, wherein the hydrophilic organic solvent is methanol or ethanol.

* * * * *